US006850590B2

(12) United States Patent
Galkin

(10) Patent No.: US 6,850,590 B2
(45) Date of Patent: Feb. 1, 2005

(54) MAMMOGRAPHY CASSETTE HOLDER FOR PATIENT COMFORT AND METHODS OF USE

(76) Inventor: Benjamin M. Galkin, 35 Ivy La., Cherry Hill, NJ (US) 08002

( * ) Notice: Subject to any disclaimer, the term of this patent is extended or adjusted under 35 U.S.C. 154(b) by 51 days.

(21) Appl. No.: 10/302,096

(22) Filed: Nov. 22, 2002

(65) Prior Publication Data

US 2003/0099325 A1 May 29, 2003

Related U.S. Application Data

(60) Provisional application No. 60/331,993, filed on Nov. 23, 2001.

(51) Int. Cl.[7] .............................................. A61B 6/04
(52) U.S. Cl. ...................................................... 378/37
(58) Field of Search .......................... 378/37, 167–170, 378/181–188, 177; 128/915

(56) References Cited

U.S. PATENT DOCUMENTS

| 5,311,883 | A | | 5/1994 | Sherman ..................... 128/846 |
|---|---|---|---|---|
| 5,377,254 | A | * | 12/1994 | Walling ....................... 378/167 |
| 5,479,927 | A | | 1/1996 | Shmulewitz ........... 128/660.09 |
| 5,541,972 | A | | 7/1996 | Anthony ...................... 378/37 |
| 5,706,327 | A | | 1/1998 | Adamkowski et al. ........ 378/37 |
| 6,049,583 | A | | 4/2000 | Galkin ......................... 378/37 |
| 6,577,702 | B1 | | 6/2003 | Lebovic et al. ............... 378/37 |
| 2003/0007597 | A1 | | 1/2003 | HIggins et al. .............. 378/37 |
| 2003/0058987 | A1 | | 3/2003 | Rick et al. .................... 378/37 |
| 2003/0194052 | A1 | | 10/2003 | Price et al. ................... 378/45 |

FOREIGN PATENT DOCUMENTS

| DE | 23 35 576 | 1/1975 |
|---|---|---|
| FR | 2 702 059 | 9/1994 |

OTHER PUBLICATIONS

Berns, E. et al., "Effect of Foam Pads on Mammography Dose Calculation", *Medical Physics, 45th Annual Meeting American Association of Physicists in Medicine*, Aug. 10–14, 2003, 2 pages.

Galkin, B.M., et al., "The Breast Pillow™: A mammogaphy device for reducing patient discomfort and pain," 2001, 0768BR–e, 1 page.

Galkin, B.M., et al., "The Breast Pillow™: A mammography device for reducing patient discomfort and pain," *Education exhibit presented at the annual meeting of the Radiological Society of North America*, Nov. 25–30, 2001, Abstract 0768BR–e published in Supplement to Radiology, 2001, 221(P), p. 698.

Galkin, B., et al., "The Breast Pillow™: A novel device to reduce patient discomfort and pain during mammography while also measuring compression force(1)," *Med. Physics*, Aug. 2001, 28(8), SU–HH–EXH C–10, 1 page.

Galkin, B.M., et al., "The Breast Pillow™: A novel device to reduce patient discomfort and pain during mammography while also measuring compression force," *Poster exhibit presented at the annual meeting of the American Association of Physicists in Medicine*, Jul. 22–26, 2001, Abstract SU–H-H–EXH C–10 published in *Med. Phys.*, 2001, p. 1820.

* cited by examiner

*Primary Examiner*—Craig E. Church
*Assistant Examiner*—Jurie Yun
(74) *Attorney, Agent, or Firm*—Woodcock Washburn LLP

(57) ABSTRACT

Comfort devices for use with a mammography unit cassette holder comprising a compressible material that substantially conforms to patient-contact surfaces of the cassette holder are provided. Openings are included in one example for passing a mammography unit cassette through. Cassette holders for use with mammography units are also provided comprising patient-contact surfaces and a compressible material integral to said patient-contact surfaces. Methods for reducing patient discomfort during a mammogram by using these comfort devices and cassette holders are also included. Mammography units are equipped with cassette holders and comfort devices to cushion the breast during compression and also change the shape of the compressed breast for repeat imaging without patient repositioning.

68 Claims, 6 Drawing Sheets

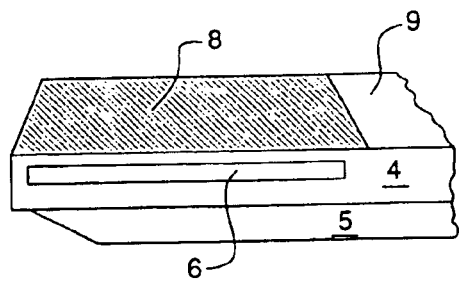
FIG. 3 - PRIOR ART
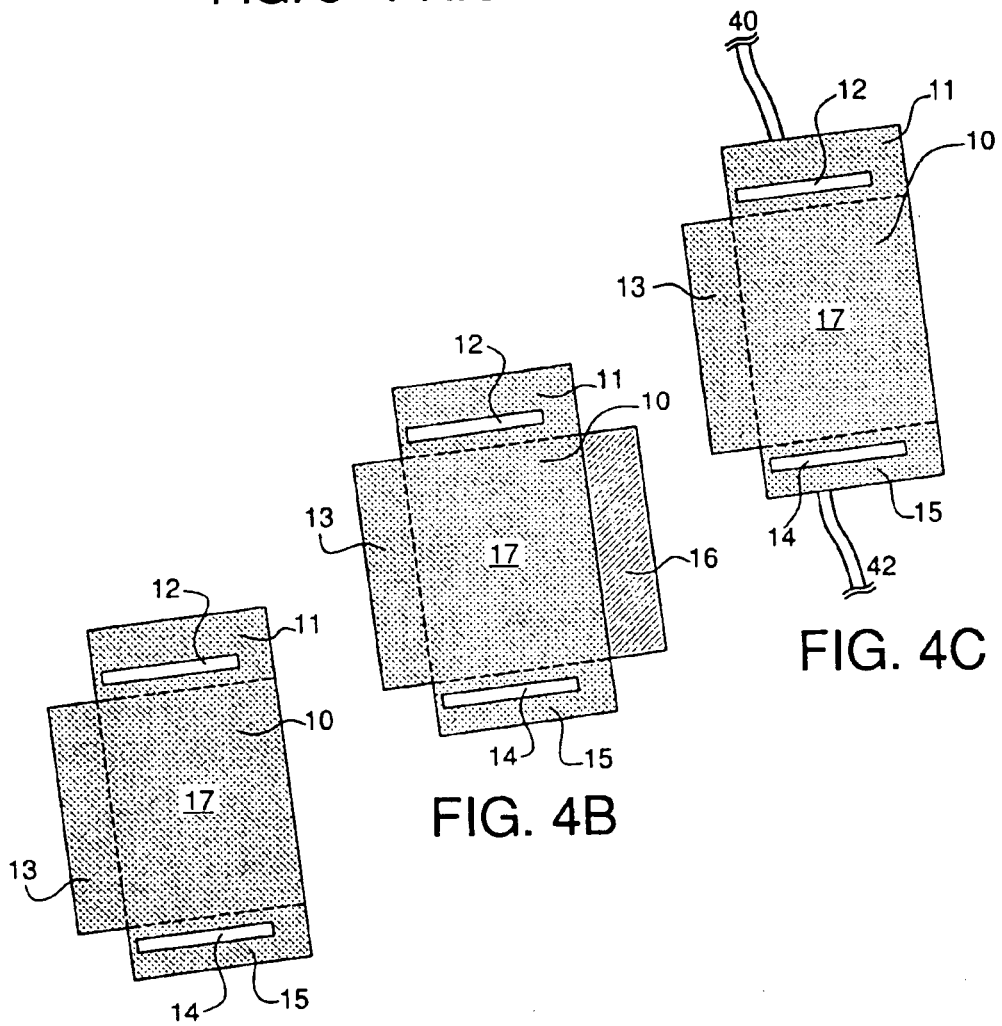
FIG. 4A
FIG. 4B
FIG. 4C

MAMMOGRAPHY CASSETTE HOLDER FOR PATIENT COMFORT AND METHODS OF USE

CROSS-REFERENCE TO RELATED APPLICATIONS

This claims the benefit of priority under 35 U.S.C. §119(e) from provisional U.S. Application Ser. No. 60/331,993, filed on Nov. 23, 2001, which is incorporated herein by reference in its entirety.

FIELD OF THE INVENTION

The present invention relates to the field of radiology and particularly to mammography. More specifically, the present invention relates to devices and methods for reducing patient discomfort and pain during mammography.

BACKGROUND OF THE INVENTION

Mammography is the process of obtaining x-ray images of the human breast for diagnosis or surgery. It involves positioning a patient's breast in a desired orientation against a cassette holder of a mammography unit (also known as a "bucky"), compressing the breast with a compression device, and then exposing the breast to x-rays to create a latent image of the breast on an image receptor. After exposure, the compression device is released. The image receptor is usually a film in contact with an intensifying screen contained within a cassette. The cassette is inserted into a cassette holder before every image is taken and removed after every image. The film is removed from the cassette and developed to produce a radiographic image of the breast.

A complete mammographic study usually involves at least two x-ray exposures of each breast. One exposure is a craniocaudal view in which the breast is compressed in a superior-inferior direction, i.e., from the direction of the patient's head downward, against a tube-side surface of the cassette holder. The plane of the tube-side surface of the cassette holder is parallel to the floor and the x-ray beam is directed vertically downward. A second exposure is a lateral or oblique view in which the breast is compressed mediolaterally, i.e., from the direction of the patient's midline sidewise, against the tube-side surface of the cassette holder which is angled, along with the axis of the x-ray beam, relative to the floor.

The compression device includes a rectangular flat plate, called a compression paddle or a compression plate, which is attached to the mammography unit between an x-ray tube assembly and the cassette holder. The edges of the paddle or plate are turned upward away from the cassette holder to provide a smooth curved surface for patient comfort. The compression paddle is usually made of thin, light-transparent, plastic that absorbs only a small fraction of the incident x-ray beam. The compression paddle is moved either manually or by power drive to apply a compression force to the breast, thereby flattening the breast against the cassette holder to a near uniform thickness. U.S. Pat. No. 6,049,583 issued to the present inventor discusses methods and apparatus for measuring compression force in mammography. After x-ray exposure, the compression force is released for patient comfort.

To properly position the patient's breast in a desired orientation, a technologist is guided by a light beam originating from the x-ray tube assembly that passes through a collimator and the compression paddle and illuminates the area of the cassette holder that will be exposed to x-rays, i.e., the imaging area. As is well known in the field, to properly position the breast, the patient's chest wall or other regions of the body, depending on the desired view, are brought into tight contact with the rigid surfaces of the cassette holder, its edges, and corners. This procedure has the effect of forcing the patent's anatomy to contour to the shape of the cassette holder, which often causes patient discomfort and pain.

Oftentimes, overlapping internal structures are present within the breast tissue that can obscure their delineation in a radiographic image. As a result, it is often necessary to reposition the breast slightly in order to arrive at a diagnosis. This requires repositioning the patient for each view with the attendant discomfort.

During positioning, compressing, and imaging, parts of the patient's body come into contact with the cassette holder. The cassette holder is a rectangular, box-like device that has a flat tube-side surface against which the breast is compressed, a flat outer surface along one edge of the tube-side surface which contacts the patient's chest wall or torso, and two flat side surfaces opposite each other along the other edges that can come into contact with other parts of the patient's anatomy such as the underarm and axilla. Each of the side surfaces has an opening, typically rectangular, to a cassette tunnel. The openings are used for insertion and removal of the cassette. The tube-side surface includes an imaging area, which is transparent to x-rays, located directly above the cassette as it resides in the cassette holder, and where the breast is positioned during imaging, and a solid section which is not transparent to x-rays. Within the cassette holder is an antiscatter grid assembly. The cassette holder is held in position on the x-ray unit by slidably engaging to a support member. Because the surfaces of the cassette holder may come into contact with blood or other infectious material, they must be able to withstand contact with the chemical agents usually used for disinfecting purposes. Cassette holders come in different sizes depending on the size film to be used.

In U.S. Pat. No. 5,541,972 by Anthony, disposable sanitary cushioning strips that are attached to the outside of the cassette holder are described. The strips are intended to be replaced between patients. The strips are placed to provide cushioning only along the outer surface of the cassette holder, and its edges and corners, where the patient's torso contacts the cassette holder. The Anthony invention, therefore, provides only limited relief for the patient since it does not cushion the breast from contact with the tube-side surface of the cassette holder.

Others in the art use a radiolucent pad, the MammoPad®, supplied by BioLucent, Inc., that is placed on the tube-side surface of the cassette holder and is folded over to the outer surface of the cassette holder facing the patient's torso. The pad is held in position by a peel-off layer of adhesive that covers the underside. This device, however, does not cushion the underarm or axilla areas for mediolateral or lateral views unless it is removed and repositioned. Moreover, if it is repositioned for these views, it blocks access to an opening to the cassette tunnel. In addition, a new pad is used for each patient, and many mammography facilities find the cost per pad to be prohibitive under current third party reimbursement schedules.

In U.S. Pat. No. 5,311,883 to Sherman, a sanitary shield for dedicated mammography apparatus is discussed. According to Sherman, the shields are made using known vacuum molding techniques. Therefore, although the shields may be flexible to a certain extent, they are not compressible and would not provide cushioning or reduction of discomfort to a patient.

In U.S. Pat. No. 5,479,927 to Shmulewitz, a gel pad that can be used in conjunction with conventional mammography equipment is discussed. The gel pad is located on the underside of a compression plate and fails to cushion the breast from either the tube-side surface or the outer surface of the cassette holder.

There remains a great need for comfort devices for use during mammography which can minimize or eliminate the pain and discomfort experienced by the patient. To be useful in clinical practice such devices must also not add significantly to the cost of the examination.

SUMMARY OF THE INVENTION

Mammography comfort devices and methods for reducing patient discomfort and pain during mammography are provided by the present invention. Such devices cushion the patient against the surfaces of the cassette holder that cause patient discomfort and pain. In one embodiment, a cassette holder is constructed with a compressible material, preferably a compressible matrix material, that is integral with surfaces of the cassette holder that contact a patient. The compressible material is preferably x-ray transparent. In a preferred embodiment, the compressible material is a low Z elastic compressible material.

The compressible material optionally comprises at least one chamber for entrapping air. It is understood that air can be permanently trapped in the chamber or forced in and released as needed. In one example, a gas inlet manifold provides pressurized gas, i.e. air, to the compressible material for inflation and a gas outlet manifold provides a route for venting the pressurized gas. The thickness of the chamber when filled with air is, for example, between at least approximately 5 millimeters and approximately 20 millimeters. Upon compression, a portion of a chamber that was approximately 5 millimeters when filled with air, for example, would have a thickness of approximately 1 millimeter. When the compressible material is non-porous, it is suitable to withstand disinfecting chemicals. The compressible material may comprise a plurality of chambers which entrap a gas permanently or have the ability to retain and release the gas.

Cassette holders in accordance with the present invention, in one example, comprise an imaging area which is made with a first compressible material which is transparent to x-rays over the mammography useful kVp range. The remaining patient-contact surfaces, which may include an outer surface, a first side surface, and a second side surface, are made with a second compressible material which is not necessarily transparent to x-rays. Cassette tunnel openings of cassette holders in accordance with the present invention are provided to ensure insertion and removal of mammography cassettes are not impeded.

In another embodiment, a comfort device, used in conjunction with a cassette holder, comprises a compressible material configured to define a cavity for containing the cassette holder which conforms to patient-contact surfaces of a cassette holder. Comfort devices are fabricated with compressible material which is transparent to x-rays over the mammography useful kVp range. One embodiment of the invention comprises a low Z elastic compressible matrix material contoured to stretch over the cassette holder's tube-side surface, outer surface, and side surfaces, edges and corners defined thereby. The sections that cover the side surfaces are configured so that they do not block the cassette tunnel. In a preferred embodiment, all of the surfaces that can come into contact with the patient are non-porous. The compressible material is transparent to x-rays over the mammography useful kVp range. The compressible material, preferably a matrix material, optionally comprises at least one chamber for entrapping air. It is understood that air can be permanently trapped in the chamber or forced in and released as needed. The thickness of the chamber when filled with air is, for example, between at least approximately 5 millimeters and approximately 20 millimeters. Upon compression, a portion of a chamber that was approximately 5 millimeters when filled with air, for example, would have a thickness of approximately 1 millimeter. When the compressible material is non-porous, it is suitable to withstand disinfecting chemicals. The compressible material may comprise a plurality of chambers which entrap a gas permanently or have the ability to retain and release the gas.

Methods for reducing patient discomfort during mammography comprise securing a cassette holder to a mammography unit where the cassette holder comprises patient-contact surfaces and a compressible material integral to the patient-contact surfaces. The compressible material is transparent to x-rays. A patient's breast is then positioned on a tube-side surface of the cassette holder and compression of the breast against the tube-side surface occurs.

Methods for reducing patient discomfort in accordance with another aspect of the present invention include securing a comfort device over a cassette holder to a mammography unit, positioning a patient such that the comfort device is disposed between the patient and patient-contact surfaces, and administering a mammogram.

In a further aspect of the present invention methods for shaping a patient's breast during a mammogram without repositioning comprise securing a cassette holder to a mammography unit wherein the comfort device comprises an inflatable chamber; an inlet manifold operatively associated with the gas source for receiving the gas and supplying the gas to the cassette holder; and an outlet manifold operatively associated with the cassette holder for receiving the gas from the cassette holder; introducing a gas into the inflatable chamber; positioning the breast on the inflatable chamber; compressing the breast forming a first shape; and imaging the first shape of the breast. Further, a portion of the gas can be released to result in the breast forming a second shape; and then the second shape of the breast can be imaged. Optionally, additional gas can be introduced to result in the breast forming a second shape and then the second shape can be imaged. Comfort devices comprising an inflatable chamber; an inlet manifold operatively associated with the gas source for receiving the gas and supplying the gas to the comfort device; and an outlet manifold operatively associated with the comfort device for receiving the gas from the cassette holder are also suitable for methods of shaping a patient's breast without repositioning.

BRIEF DESCRIPTION OF THE DRAWINGS

The present invention will be better understood, and its numerous objects and advantages will become apparent to those skilled in the art by reference to the following detailed description of the invention when taken in conjunction with the following drawings, in which:

FIG. 3 is an enlarged schematic view of a typical cassette holder;

FIG. 4A is a top view of a comfort device in accordance with an embodiment of the invention, flattened to show sections for covering patient-contact surfaces of a cassette holder; FIG. 4B depicts the comfort device of FIG. 4A comprising an optional section for holding the comfort device in place on the cassette holder in accordance with an embodiment of the present invention; FIG. 4C depicts the comfort device of FIG. 4A comprising optional fasteners for holding the comfort device in place on the cassette holder in accordance with an embodiment of the present invention;

DETAILED DESCRIPTION OF ILLUSTRATIVE EMBODIMENTS

Figure 1:
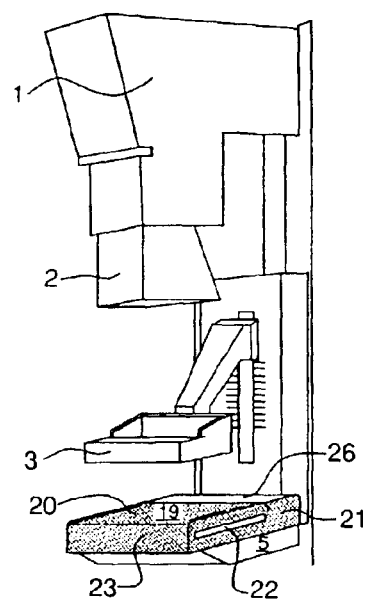
FIG. 1 is a schematic oblique view of a section of a mammography unit illustrating the position of a cassette holder relative to a compression paddle in accordance with an embodiment of the present invention.

This invention describes devices and methods used to minimize and/or eliminate patient discomfort and pain during mammography. In accordance with the invention, surfaces that contact the patient during mammography comprise compressible material, preferably low Z elastic compressible material. For example, a cassette holder for use with a conventional mammography x-ray unit would comprise compressible surfaces that are integral to the cassette holder. Edges and corners of the cassette holder rounded with a compressible material also to minimize patient discomfort and pain. Cassette holders in accordance with the present invention have at least one compressible surface, preferably a tube-side surface, which changes shape upon compression. Other compressible surfaces may include an outer surface, a first side surface, and a second side surface. Side surfaces are provided with openings for unimpeded placement of cassettes within the cassette holder. Though surfaces are compressible, they do not interfere with insertion and removal of cassettes or the functioning of an antiscatter grid. In one example, the compressible material further comprises non-porous material to provide a surface suitable for disinfecting.

In another example, by reference to an existing cassette holder, a comfort device comprising compressible material which is transparent to x-ray is stretched over the cassette holder to ensure the patient-contact surfaces are cushioned. The patient-contact surfaces include, but are not limited to a tube-side surface, an outer surface, a first side surface, and a second side surface. Upon positioning of the patient's breast on an imaging area of the tube-side surface and subsequent compression, the patient's body is then protected from the rigid surfaces and sharp edges of the bare cassette holder by the presence of the comfort device.

Compressible material may include, but is not limited to, polyethylene materials, polypropylene materials, and rubber foam. Forms of compressible material include, but are not limited to foam, bubble wrap, anti-static, air core, nylon barrier core, tubing, and matrix. For example, low density polyethylene foams provide resiliency and cushioning characteristics suitable to reduce patient discomfort. Bubble wrap, is a further example of material that is compressible and provides cushioning. Furthermore, various forms of high and low density polyethylenes could comprise at least one chamber suitable for inflation. Although rubber foam is compressible, it is preferably suitable for surfaces other than the tube-side due to its potential to interfere with the transmission of x-rays.

Comfort devices in accordance with the present invention are amenable to a wide variety of cassette holder shapes and sizes. Given the adaptability of various compressible materials, comfort devices are constructed to fit around various-sized cassette holders and contain openings to permit insertion and removal of various-sized cassettes. Although allowance is made for the use of conventional x-ray films, it is understood that solid state imaging x-ray systems, which do not comprise cassette tunnels, comprising rigid surfaces and sharp edges and corners that contact the patient would also be amenable to embodiments of the present invention.

Figure 2:
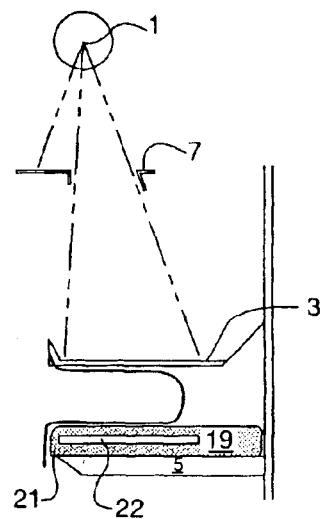
FIG. 2 is a schematic lateral view of FIG. 1 depicting a compressed breast positioned on a cassette holder showing the edge of the cassette holder in contact with the patient's torso.

Referring now to the drawings wherein reference numerals refer to like elements, FIGS. 1 and 2 depict two views of a mammography unit in accordance with an embodiment of the present invention having an x-ray tube 1 that produces x-ray beams (not numbered) connected to a cone 2 that houses a collimator 7. The collimator 7 restricts the size and shape of the x-ray beams in any plane perpendicular to the axis of the x-ray beam. The x-ray beam also passes through a compression paddle 3. Below the compression paddle 3 is a cassette holder 19, which comprises a tube-side surface containing an imaging area 20 and a solid area 26, and a cassette tunnel opening 22. Generally, a cassette tunnel located below the imaging area houses an antiscatter grid and a cassette. The cassette holder 19 is held in place by a support member 5 and slidably engages with a support column (not numbered). X-ray beams pass through imaging area 20 to expose a film in the cassette. The solid area 26 is typically not transparent to x-ray beams and secures the cassette holder to the support column. A patient's breast (not numbered) is positioned on the imaging area 20 of the tube-side surface of the cassette holder 19 and is compressed by the compression paddle 3.

FIG. 3 in an enlarged schematic view of a typical cassette holder 4 positioned on a support member 5, comprising a cassette tunnel 6, an imaging area 8, and a solid area 9.

FIG. 4A is a top view of a comfort device 17 in accordance with the invention, flattened, to show sections 10, 11, 13, and 15 for covering patient-contact surfaces of a cassette holder, depicted, for example, in FIG. 3. In one example, a comfort device 17 is fabricated with a compressible material. Compressible material is preferably low Z elastic matrix material that entraps air. The material can comprise a cushion of air which permanently entraps air. The material can also comprise a plurality of cushions. Alternatively, the material can comprise at least one inflatable chamber to contain air that can be forced or pumped into the comfort device. The compressible material comprises a section 10 for covering the imaging area 8. The device also comprises sections 11, 13, and 15 for covering other surfaces of the cassette holder that can come into contact with a patient during mammography. Sections 11 and 15 have openings 12 and 14, typically rectangular, to facilitate the insertion and removal of a cassette in the cassette holder. In one example, adhesive strips are suitable for securing the underside of the comfort device to the cassette holder.

In another example, as shown in FIG. 4B, the comfort device of FIG. 4A is depicted with optional section 16 which is an extension of the compressible material that can be adapted with methods for retaining the compressible material in place on the cassette holder. Furthermore, there is no limitation on the material used to fabricate section 16. Although compressible material may be used to facilitate ease of manufacture of the comfort device, it is understood that oftentimes section 16 need not be x-ray transparent, because x-ray beams do not need to penetrate that area, nor compressible, because a patient typically does not contact that area. Section 16 can be integral with the comfort device or attached separately.

In yet a further example, as shown in FIG. 4C, the comfort device of FIG. 4A is depicted with optional fasteners 40 and 42 which secure the device by wrapping around the underside of the support member 5. One fastener is shown on each opposite side of the comfort device, however, it is contemplated that multiple fasteners are suitable for attaching along either side. Furthermore, one fastener can be used which secures to an opposite side of the comfort device.

In one example, fasteners can be straps that meet underneath the support member and tie together. In another example, fasteners can engage with each other using hook and loop fasteners. Yet another embodiment includes fasteners that can be one-piece elastic bands which are fixed to opposite sides of the comfort device. The fasteners can be fabricated of any material suitable for fastening and unfastening. For ease of manufacture, however, it may be desirable to fabricate the fasteners out of the compressible material of the comfort device. Fasteners can be integral with the comfort device or attached separately.

Figure 5A:
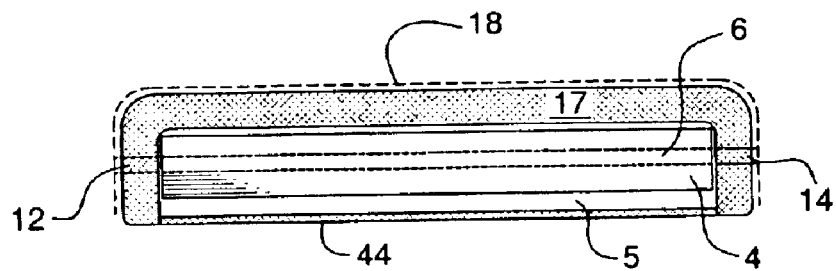
FIG. 5A is a schematic cross-section of a cassette holder assembled with a comfort device in accordance with an embodiment of the invention.
Figure 5B:
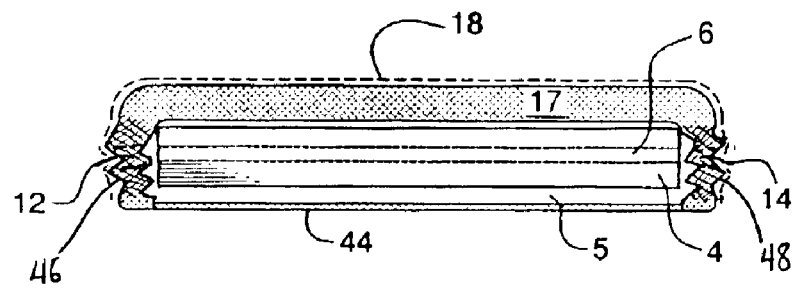
FIG. 5B is another schematic cross-section of a cassette holder assembled with a comfort device.

FIG. 5A is a schematic cross-section of a cassette holder 4 assembled with a comfort device 17 in accordance with another embodiment of the invention. Cassette tunnel 6 is accessible through openings 12 and 14. In one embodiment, the comfort device comprises a compressible material having openings 12 and 14 and a bottom 44 such that the comfort device conforms, essentially enveloping, around both patient-contact surfaces of the cassette holder 4 and the bottom of the support member 5. FIG. 5B is a schematic cross-section of a cassette holder 4 assembled with a comfort device comprising gussets 46 and 48 to permit the device to expand around both the cassette holder and the support member. Openings 12 and 14 are not limited in shape. For example, openings 12 and 14 could be created by scoring the gusseted area to create slits for permitting cassettes to pass through. An outer surface (not shown) also can comprise a gusseted area to facilitate expansion of the comfort device around the cassette holder and support member. In another example, openings 12 and 14 could be rectangular. Preferably the compressible material exhibits elastic properties such that the elastic property of the comfort device keeps it in place.

In one example, the compressible material comprises non-porous surfaces 18 that are resistant to the chemical agents usually used for disinfecting purposes. This obviates the need to replace the compressible material between patients. To comply with regulations, it is merely necessary to disinfect the surface after each patient in the usual manner. When used this way, the cost of the compressible material can be spread over many cases which makes its use cost effective under current reimbursement schedules.

Figure 6:
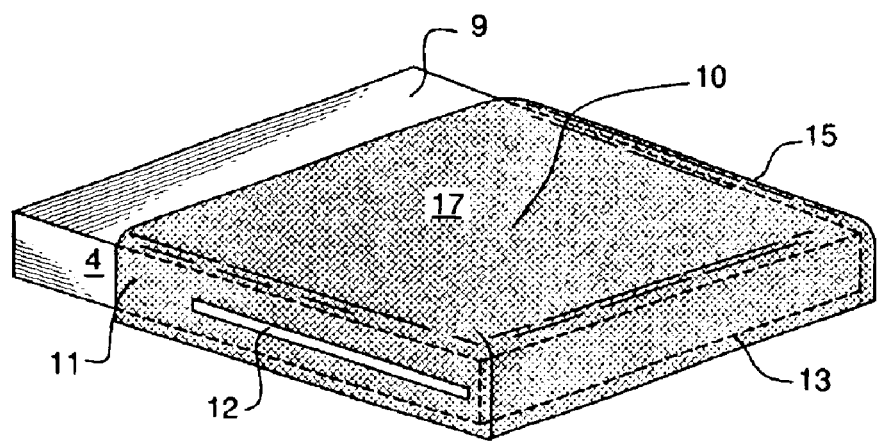
FIG. 6 is a schematic angular view of a cassette holder assembled with a comfort device in accordance with an embodiment of the invention.

FIG. 6 is a schematic angular view of a cassette holder 4 assembled with a comfort device 17 in accordance with an embodiment of the invention. The comfort device 17, in one embodiment, comprises sections that cover patient-contact surfaces, such as an imaging area section 10 that covers the imaging area of the cassette holder 4, but not the solid area, 9 and an outer section 13 to cover the side of the cassette holder that contacts the patient's torso. A first section 11 contains a first opening 12 which substantially coincides with a first cassette tunnel opening when the device 17 is in place on the cassette holder 4. A second section 15 contains a second opening (not shown) which substantially coincides with a second cassette tunnel opening when the device 17 is in place on the cassette holder 4. As discussed in reference to FIG. 4A, an optional extension to the comfort device covers solid area 9. As discussed in reference to FIG. 4B, it is optional to attach one fastener or a plurality of fasteners to the first section 11 and the second section 15.

In another preferred embodiment of this invention, a mammography cassette holder has compressible surfaces and rounded corners and edges that are integral to the cassette holder itself. Thus, the cassette holder itself contours to the patient's anatomy during positioning and compression. The compressible sections do not block access to either side of the cassette tunnel. The compressible sections include but are not limited to a tube-side surface against which the breast is compressed including the region that overlays the image receptor, an outer surface that can come into contact with the patients torso, and side surfaces that can come into contact with other parts of the patient's anatomy, such as the axilla and underarm regions. In one example, the compressible section over the image receptor is made of material that is transparent to x-rays and does not compromise image quality. The surface of the compressible material that contacts the patient can be nonporous and resistant to the chemical agents usually used for disinfecting purposes. This essentially eliminates the need to replace the compressible material between patients and the cost associated therewith. Alternatively, porous material can be used in conjunction with a thin, disposable x-ray transparent sanitary device that covers the compressible cassette holder during a mammogram.

Figure 7:
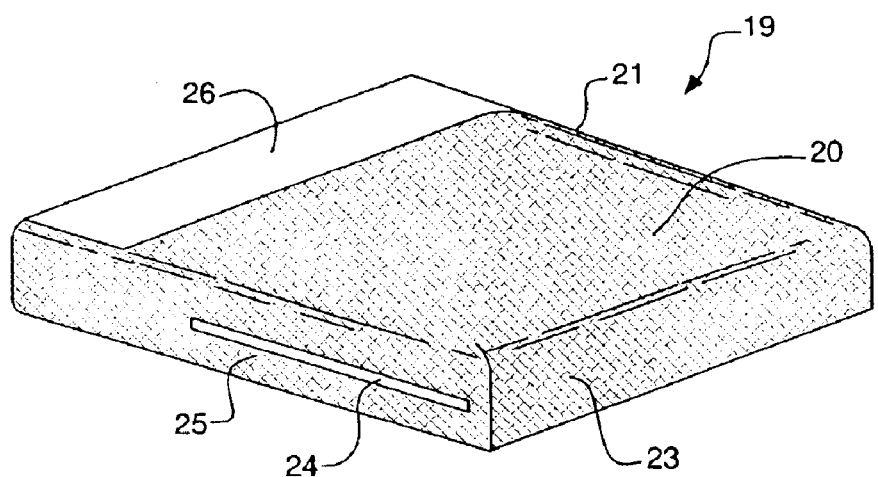
FIG. 7 is a schematic angular view of a cassette holder adapted in accordance with an embodiment of the invention.

FIG. 7 is a schematic angular view of a cassette holder 19 adapted in accordance with an embodiment of the invention. The cassette holder 19 comprises compressible material, which is preferably a low Z matrix material, comprising a tube-side surface 20, an outer surface 23, a first side surface 21 containing a first opening (not shown) to the cassette tunnel, a second side surface 25 containing a second opening 24. A solid area 26 secures to a support column of a mammography unit. The material optionally comprises a nonporous surface. By incorporating the compressible material into the cassette holder itself, the need for an add-on cushioning device is obviated.

Figure 8C:
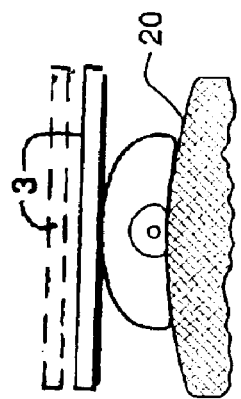
FIG. 8C shows the cassette holder of FIG. 8A upon inflation of the cassette holder.
Figure 8B:
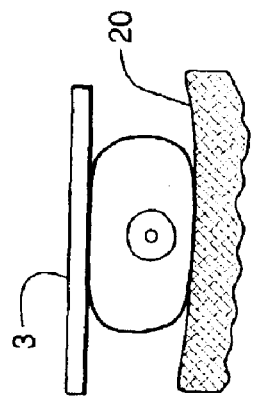
FIG. 8B shows the cassette holder of FIG. 8A upon deflation of the cassette holder.
Figure 8A:
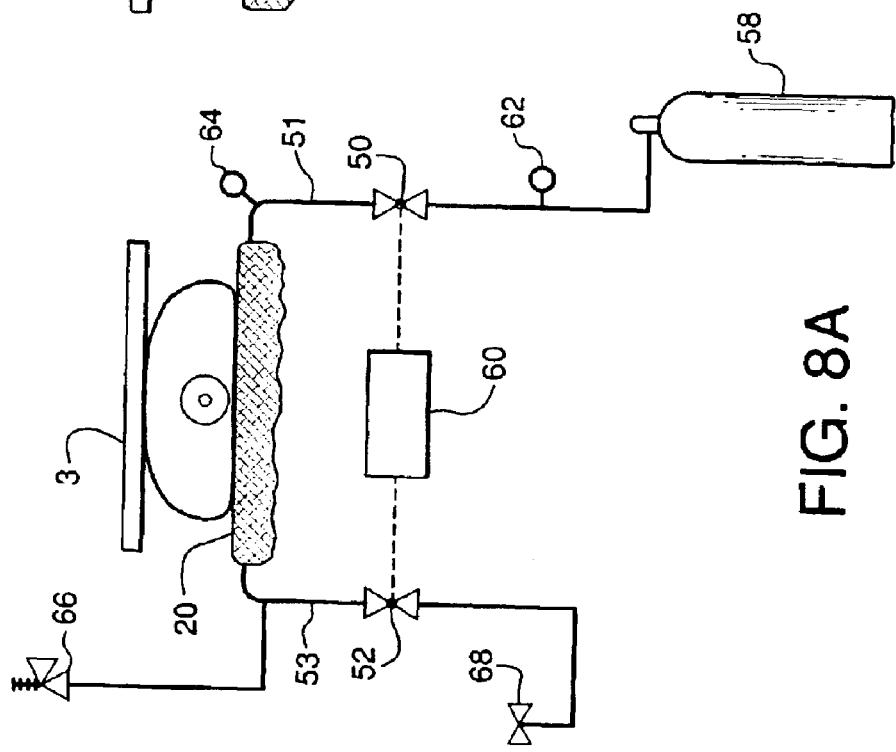
FIG. 8A a rear sectional diagrammatic view illustrating a breast in position on an embodiment of the cassette holder of FIG. 1 relative to a compression paddle in accordance with an embodiment of the present invention.

FIG. 8A depicts a side view illustrating a breast in position on a cassette holder relative to a compression paddle in accordance with an embodiment of the present invention. In FIG. 8A, a tube-side surface 20 of a cassette holder contains a volume of fluid against which a breast is cushioned during compression by a compression paddle 3.

The volume of fluid contained in the cassette holder can be adjusted. A fluid source 58 supplies a fluid, preferably a gas, for example air, which is passed through line 51 into the cassette holder. The cassette holder can receive the fluid at any part of the cassette holder that is convenient. The tube-side surface 20 is inflatable, and other sides of the cassette holder can be inflatable, as desired.

Fluid pressure is measured by a first pressure gauge 62 and a second pressure gauge 64. A first manifold 50 receives fluid from source 58 and supplies the cassette holder. Fluid is released from the cassette holder through line 53. A second manifold 52 receives the fluid from the cassette holder. A pressure relief valve 66 operatively connected with line 53 is provided for safety and protecting the cassette holder from over-inflation. The second manifold 52 reduces pressure in the cassette holder, for example, by venting through vent 68. It is also possible that the second manifold 52 is operatively associated with a vacuum source to facilitate reducing pressure in the cassette holder. A controller 60 can be operatively associated with the first manifold 50 and the second manifold 52. In one embodiment, the controller can be operated from an x-ray shielded position. For example, the controller can be associated with a remote control panel from which a technician operates the device. Alternatively, the controller can be operated from a position unshielded from x-rays. For example, the controller can be operated locally at the mammography unit itself.

Source 58 is any container suitable for containing a fluid. For example, a gas can be stored in compressed form in a suitable compressed gas cylinder, which is potentially housed within the mammography unit. It is noted that that such a gas source could also be an external tank which is in fluid communication with the mammography unit via gas lines or tubing.

FIG. 8B shows the cassette holder of FIG. 8A upon reduction of the volume of fluid in the cassette holder in accordance with an embodiment of the present invention. The reduction in pressure results in an approximately concave shape to the tube-side surface 20. The change in shape of the tube-side surface permits the breast to change shape without the need for repositioning. As a result, another image can be obtained without having to release the compression paddle 3, reposition the breast, and then compress the breast again.

FIG. 8C shows the cassette holder of FIG. 8A upon addition of fluid to the cassette holder in accordance with an embodiment of the present invention. The increased volume of fluid in the cassette holder results in an approximately convex shape to the tube-side 20. The change in shape of the tube-side permits the breast to change shape without the need for repositioning. As a result, another image can be obtained without having to release the compression paddle 3, reposition the breast, and then compress the breast again. FIG. 8C also depicts the compression paddle 3 displaced in the direction of the x-ray tube from its position in FIGS. 8A and 8B to compensate whenever desirable for the additional compression force exerted on the breast by the increased volume of fluid in the cassette holder. The magnitude of the displacement can be controlled automatically by sensors in the fluid lines.

Figure 9C:
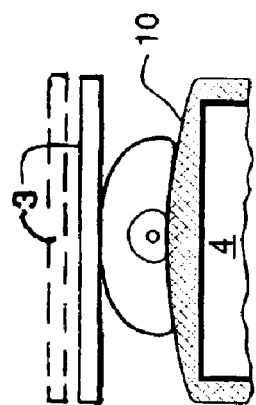
FIG. 9C shows the comfort device of FIG. 9A upon inflation of the cassette holder.
Figure 9B:
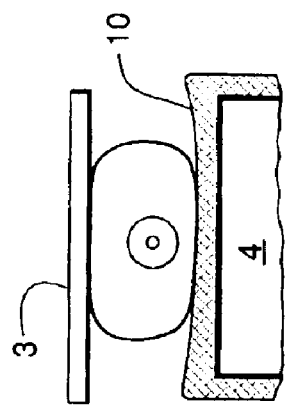
FIG. 9B shows the comfort device of FIG. 9A upon deflation of the comfort device.
Figure 9A:
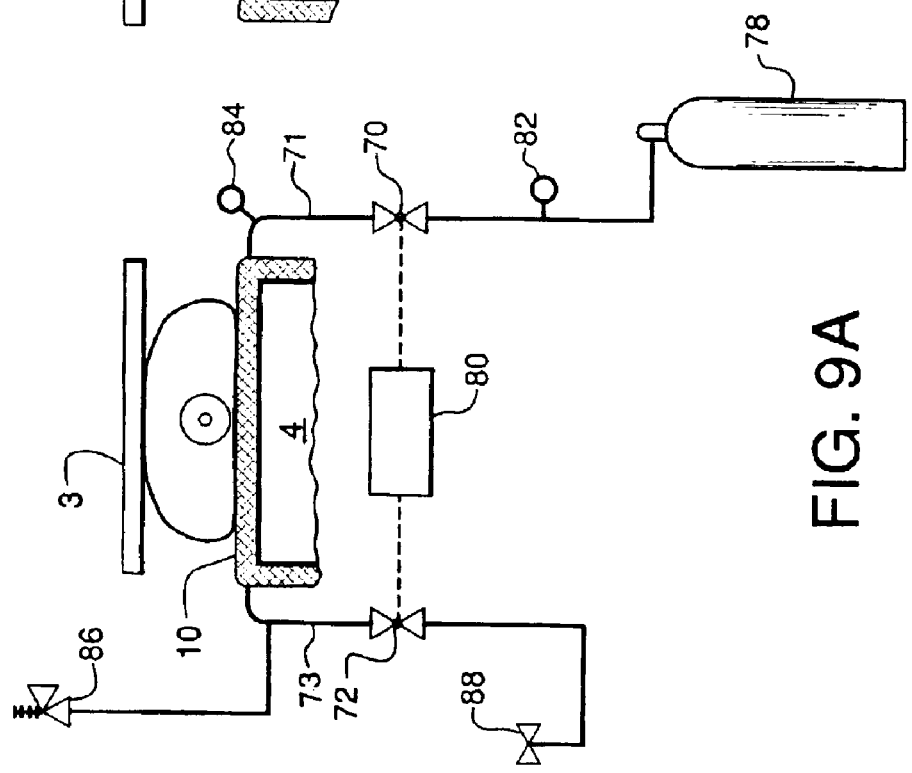
FIG. 9A is a rear sectional diagrammatic view illustrating a breast in position on an embodiment of the comfort device of FIG. 6 relative to a compression paddle in accordance with an embodiment of the present invention.

FIG. 9A depicts a side view illustrating a breast in position on a cassette holder relative to a compression paddle in accordance with an embodiment of the present invention. In FIG. 9A, a tube-side section 10 of a comfort device 17 which is in position on a cassette holder 4 contains a volume of fluid against which a breast is cushioned during compression by a compression paddle 3. The volume of fluid contained in the comfort device 17 can be adjusted. In a preferred embodiment, a gas source 78 supplies a gas, for example air, which is passed through gas line 71 into the comfort device. The comfort device can receive the gas at any part of the comfort device that is convenient. The tube-side section 20 is inflatable, and other sides of the comfort device can be inflatable as desired.

Pressure of the gas is measured by a first pressure gauge 82 and a second pressure gauge 84. A first manifold 70 receives the gas from the gas source 78 and supplies the comfort device 17 with the gas. Gas is released from the comfort device 17 through gas line 73. A second manifold 72 receives the gas from the comfort device 17. A pressure relief valve 86 operatively connected with gas line 73 is provided for safety and protecting the comfort device 17 from over-inflation. The second manifold 72 reduces pressure in the comfort device 17, for example, by venting through vent 88. It is also possible that the second manifold 72 is operatively associated with a vacuum source to facilitate reducing pressure in the comfort device 17. A controller 80 can be operatively associated with the first manifold 70 and the second manifold 72. In one embodiment, the controller can be operated from an x-ray shielded position. For example, the controller can be associated with a remote control panel from which a technician operates the device. Alternatively, the controller can be operated from a position unshielded from x-rays. For example, the controller can be operated locally at the mammography unit itself.

Gas source 78 is any container suitable for containing a gas. For example, the gas can be stored in compressed form in a suitable compressed gas cylinder, which is potentially housed within the mammography unit. It is understood that that the gas source could also be an external tank which is in fluid communication with the mammography unit via gas lines or tubing.

FIG. 9B shows the comfort device of FIG. 9A upon reduction of the volume of gas in the comfort device in accordance with an embodiment of the present invention. The reduction in pressure results in an approximately concave shape to the tube-side section 10. The change in shape of the tube-side section 10 permits the breast to change shape without the need for repositioning. As a result, another image can be obtained without having to release the compression paddle 3, reposition the breast, and then compress the breast again.

FIG. 9C shows the comfort device of FIG. 9A upon addition of gas to the comfort device in accordance with an embodiment of the present invention. The increased volume of gas in the comfort device results in an approximately convex shape to the tube-side section 10. The change in shape of the tube-side section 10 permits the breast to change shape without the need for repositioning. As a result, another image can be obtained without having to release the compression paddle 3, reposition the breast, and then compress the breast again. FIG. 9C also depicts the compression paddle 3 displaced in the direction of the x-ray tube from its position in FIGS. 9A and 9B to compensate whenever desirable for the additional compression force exerted on the breast by the increased volume of fluid in the cassette holder. The magnitude of the displacement can be controlled automatically by sensors in the gas lines.

In one use of an embodiment of the present invention, a comfort device is stretched over a cassette holder before a mammogram begins. The patient is then positioned in the usual way except that the compressible material is now between the sensitive area of the patient and the rigid surfaces and sharp edges and corners of the cassette holder. The cushioning effect can be provided, for example, by air entrapped in the compressible material. As force is applied during patient positioning and breast compression, some of the air can be expelled thereby compressing the material. The breast is then radiographed using the regular exposure technique. Release of the force enables air to reenter the material and assume its original shape.

The compressible material preferably facilitates maintaining the material in proper position for any angulation of the primary beam. As a result, a single comfort device can remain in place for all the require views.

In another use of an embodiment of the present invention, a cassette holder with at least one surface comprising compressible material is secured to a conventional mammography unit before a mammogram begins. The patient is then positioned in the usual way and the patient's body now is cushioned against the compressible surfaces and rounded edges and corners of the cassette holder. The cushioning effect is provided, for example, by air entrapped in the compressible material. As force is applied during patient positioning and breast compression, some of the air can be expelled thereby compressing the material. The breast is then radiographed using the regular exposure technique. Release of the force enables air to reenter the material and assume its original shape.

In a further aspect of the present invention methods for shaping a patient's breast during a mammogram without repositioning comprise securing a cassette holder to a mammography unit wherein the comfort device comprises an inflatable chamber; an inlet manifold operatively associated with the gas source for receiving the gas and supplying the gas to the cassette holder; and an outlet manifold operatively associated with the cassette holder for receiving the gas from the cassette holder; introducing a gas into the inflatable chamber; positioning the breast on the inflatable chamber; compressing the breast forming a first shape; and imaging the first shape of the breast. Further, a portion of the gas can be released to result in the breast forming a second shape; and then the second shape of the breast can be imaged. Optionally, additional gas can be introduced to result in the breast forming a second shape and then the shape can be imaged. Comfort devices comprising an inflatable chamber; an inlet manifold operatively associated with the gas source for receiving the gas and supplying the gas to comfort device; and an outlet manifold operatively associated with the comfort device for receiving the gas from the cassette holder are also suitable for methods of shaping a patient's breast without repositioning.

While the invention has been described and illustrated with reference to specific embodiments, those skilled in the art will recognize that modifications and variations may be made without departing from the principles of the invention as described herein and set forth in the following claims.

What is claimed:

1. A mammography unit comprising:
   a mammography unit cassette holder, which comprises an imaging area, a first side surface substantially perpendicular to said imaging area having a first tunnel opening, a second side surface opposite said first side surface having a second tunnel opening, an outer surface substantially perpendicular to said imaging area, said first side surface, and said second side surface;
   a comfort device, which comprises a compressible x-ray transparent material configured to define a cavity for containing said mammography unit cassette holder, wherein said compressible x-ray transparent material substantially conforms to said imaging area, said first side surface, said second side surface, and said outer surface and comprises a top area; a first side area comprising a first opening having a perimeter that is shorter than a perimeter of said first side area adapted to permit a mammography unit cassette to pass therethrough, said first opening substantially coinciding with said first tunnel opening when said compressible material is assembled with said mammography unit cassette holder; and a second side area comprising a second opening having a perimeter that is shorter than a perimeter of said second side area adapted to permit a mammography unit cassette to pass therethrough, said second opening substantially coinciding with said second tunnel opening when said compressible material is assembled with said mammography unit cassette holder; and
   an x-ray source, a compression device, and a support member to which said mammography unit cassette holder is secured.

2. The mammography unit of claim 1 wherein said material comprises low Z elastic matrix material.

3. The mammography unit of claim 1 wherein said material further comprises a chamber for entrapping a fluid.

4. The mammography unit of claim 3 wherein said chamber is between at least approximately 5 millimeters and approximately 20 millimeters thick when said fluid is entrapped therein.

5. The comfort device of claim 3 wherein said fluid comprises a gas.

6. The comfort device of claim 5 wherein said gas comprises air.

7. The mammography unit of claim 1 wherein said material further comprises non-porous material.

8. The mammography unit of claim 1 wherein said material further comprises a first fastener having a first free end; and a first attached end positioned on a first side of said compressible material.

9. The mammography unit of claim 8 wherein said first free end engages with a second side of said material.

10. The mammography unit of claim 9 wherein said first free end engages with said second side through the use of a hook and loop fastener.

11. The mammography unit of claim 8 wherein said first free end is fixably attached to a second side of said material.

12. The mammography unit of claim 11 wherein said first fastener comprises elastic.

13. The mammography unit of claim 8 further comprising: a second fastener having a second free end and a second attached end positioned on a second side of said material, opposite to said first side, wherein said first free end is engagable with said second free end.

14. The mammography unit of claim 13 wherein said first end engages with said second end by use of a hook and loop fastener.

15. The mammography unit of claim 8 wherein said first fastener comprises a plurality of fasteners.

16. The mammography unit of claim 1 wherein said material further comprises a bottom that;
    substantially conforms to the underside of said support member.

17. The mammography unit of claim 16 wherein said first side surface comprises a first gusset; wherein said second side surface comprises a second gusset, and wherein said outer surface comprises a third gusset.

18. A mammography unit comprising:

a mammography unit cassette holder, which comprises an imaging area, a first side surface substantially perpendicular to said imaging area having a first tunnel opening, a second side surface opposite said first side surface having a second tunnel opening, an outer surface substantially perpendicular to said imaging area, said first side surface, and said second side surface; and a comfort device, which comprises a compressible material, which substantially conforms to said imaging area, said first side surface, said second side surface, and said outer surface and said compressible material comprises x-ray transparent material; a first side opening which substantially coincides with said first tunnel opening when said compressible material is assembled with said mammography unit cassette holder, and a second side opening which substantially coincides with said second tunnel opening when said compressible material is assembled with said mammography unit cassette holder;

an x-ray source, a compression device, and a support member to which said mammography unit cassette holder is secured.

19. The mammography unit of claim 18 wherein said compressible material further comprises a fastener.

20. The mammography unit of claim 18 wherein said compressible material further comprises:

an inlet manifold operatively associated with said comfort device to deliver a fluid to said comfort device; and an outlet manifold operatively associated with said comfort device to receive said fluid from said comfort device.

21. The comfort device of claim 20 wherein said fluid comprises a gas.

22. The comfort device of claim 21 wherein said gas comprises air.

23. A mammography unit comprising:

a mammography unit cassette holder, which comprises patient-contact surfaces comprising an imaging area; a first side surface substantially perpendicular to said imaging area, said first side surface comprising a first tunnel opening adapted to permit a mammography unit cassette to pass therethrough; and a second side surface opposite said first side surface, said second side surface comprising a second tunnel opening adapted to permit a mammography unit cassette to pass therethrough; and an outer surface substantially perpendicular to said imaging area, said first side surface, and said second side surface;

a compressible x-ray transparent material integral to said patient-contact surfaces; and an x-ray source, a compression device, and a support member to which said mammography unit cassette holder is secured.

24. The mammography unit of claim 23 wherein said material comprises low Z elastic matrix material.

25. The mammography unit of claim 23 wherein said material further comprises a chamber for entrapping a gas.

26. The mammography unit of claim 25 wherein said material further comprises:

an inlet manifold operatively associated with said cassette holder to delivering a gas to said cassette holder; and an outlet manifold operatively associated with said cassette holder to receive said gas from said cassette holder.

27. The mammography unit of claim 25 wherein said chamber is between approximately 5 millimeters and approximately 20 millimeters when gas is entrapped.

28. The mammography unit of claim 23 wherein said material further comprises non-porous material.

29. A mammography unit comprising:

a mammography unit cassette holder, which comprises an imaging area; a first side surface substantially perpendicular to said imaging area comprising a first tunnel opening adapted to permit a mammography unit cassette to pass therethrough; a second side surface opposite said first side surface comprising a second tunnel opening adapted to permit a mammography unit to pass therethrough; and an outer surface substantially perpendicular to said imaging area, said first side surface, and said second side surface;

wherein said imaging area comprises a first compressible material wherein said material is x-ray transparent; and an x-ray source, a compression device, and a support member to which said mammography unit cassette holder is secured.

30. The mammography unit of claim 29 wherein said first compressible material further comprises:

a chamber;

an inlet manifold operatively associated with said cassette holder for delivering a fluid to said chamber; and an outlet manifold operatively associated with said cassette holder for receiving said fluid from said chamber.

31. The mammography unit of claim 30 wherein said first side surface, said second side surface, and said outer surface comprise a second compressible material.

32. The mammography unit of claim 31 wherein said first side surface comprises a first tunnel opening adapted to permit a mammography unit cassette to pass therethrough; and wherein said second side surface comprises a second tunnel opening to permit a mammography unit cassette to pass therethrough.

33. The mammography unit of claim 31 wherein said first compressible material is non-porous and wherein said second compressible material is non-porous.

34. A mammography unit comprising:

a cassette holder comprising an inflatable chamber;

a source for supplying a fluid;

an inlet manifold operatively associated with said source for receiving said fluid and supplying said fluid to said cassette holder; and an outlet manifold operatively associated with said cassette holder for receiving said fluid from said cassette holder.

35. The mammography unit of claim 34 wherein said fluid is a gas.

36. The mammography unit of claim 35 wherein said gas is pressurized.

37. The mammography unit of claim 34 further comprising:

a controller operatively connected to said inlet manifold, said outlet manifold, and a pressure measuring device for controlling fluid inlet pressure.

38. The mammography unit of claim 37 wherein said controller is operated from an x-ray shielded position.

39. The mammography unit of claim 37 wherein said controller is operated from an x-ray unshielded position.

40. The mammography unit of claim 37 further comprising a vent operatively associated with said outlet manifold.

41. The mammography unit of claim 37 further comprising a vacuum source operatively associated with said outlet manifold.

42. A mammography unit comprising:
a comfort device comprising an inflatable chamber;
a cassette holder;
a gas source for supplying a gas;
an inlet manifold operatively associated with said gas source for receiving said gas and supplying said gas to said cassette holder; and
an outlet manifold operatively associated with said cassette holder for receiving said gas from said cassette holder.

43. The mammography unit of claim 42 wherein said gas is air.

44. The mammography unit of claim 42 wherein said gas is pressurized.

45. The mammography unit of claim 42 further comprising:
a controller operatively connected to said inlet manifold, said outlet manifold, and a pressure measuring device for controlling gas inlet pressure.

46. The mammography unit of claim 45 wherein said controller is operated from an x-ray shielded position.

47. The mammography unit of claim 45 wherein said controller is operated from an x-ray unshielded position.

48. The mammography unit of claim 45 further comprising a vent operatively associated with said outlet manifold.

49. The mammography unit of claim 45 further comprising a vacuum source operatively associated with said outlet manifold.

50. A method for reducing patient discomfort during a mammogram comprising:
securing a cassette holder to a mammography unit wherein said cassette holder comprises:
patient-contact surfaces;
an inflatable chamber; and
a compressible x-ray transparent material integral to said patient-contact surfaces;
positioning a patient's breast on a tube-side surface; and
compressing said breast against said tube-side surface.

51. The method of claim 50 further comprising inflating said cassette holder with a fluid to reshape said breast.

52. The method of claim 51 further comprising releasing said fluid.

53. The method of claim 51 comprising inflating said tube-side surface.

54. The method of claim 51 wherein said fluid comprises a gas.

55. The comfort device of claim 54 wherein said gas comprises air.

56. The method of claim 50 wherein said compressible material is non-porous.

57. The method of claim 50 further comprising placing a disposable x-ray transparent sanitary shield over the patient-contact surfaces.

58. A method for reducing patient discomfort during a mammogram comprising:
securing a comfort device over a mammography unit cassette holder wherein said comfort device comprises:
a compressible x-ray transparent material configured to define a body for containing said cassette holder, said material having a first opening adapted to permit a mammography unit cassette to pass therethrough; and
a second opening adapted to permit a mammography unit cassette to pass therethrough, wherein said material substantially conforms to patient-contact surfaces of said mammography unit cassette holder; and
securing said mammography unit cassette holder to a support member of a mammography unit:
positioning a patient such that the comfort device is disposed between said patient and said patient-contact surfaces; and
administering a mammography comprising compressing a breast of said patient.

59. A method for shaping a patient's breast during a mammogram without repositioning comprising:
securing a cassette holder to a mammography unit wherein said cassette holder comprises:
an inflatable chamber;
an inlet manifold operatively associated with a source for receiving a fluid and supplying said fluid to said cassette holder; and
an outlet manifold operatively associated with said cassette holder for receiving said fluid from said cassette holder;
introducing said fluid into said inflatable chamber;
positioning said breast on said inflatable chamber;
compressing said breast forming a first shape; and
imaging said first shape of said breast.

60. The method of claim 59 further comprising: releasing a portion of said fluid to result in said breast forming a second shape; and imaging said second shape of said breast.

61. The method of claim 60 further comprising:
introducing additional fluid to result in said breast forming a third shape; and
imaging said third shape.

62. The method of claim 59 further comprising: introducing additional fluid to result in said breast forming a second shape; and imaging said second shape.

63. A method for shaping a patient's breast during a mammogram without repositioning comprising:
securing a comfort device to a cassette holder wherein said comfort device comprises:
an inflatable chamber;
an inlet manifold operatively associated with a gas source for receiving a gas and supplying said gas to said comfort device; and
an outlet manifold operatively associated with said comfort device for receiving said gas from said comfort device;
introducing said gas into said inflatable chamber;
positioning said breast on said inflatable chamber;
compressing said breast forming a first shape;
imaging said first shape of said breast.

64. The method of claim 63 further comprising: releasing a portion of said gas to result in said breast forming a second shape; and imaging said second shape of said breast.

65. The method of claim 64 further comprising: introducing additional gas to result in said breast forming a third shape; and imaging said third shape.

66. The method of claim 63 further comprising: introducing additional gas to result in said breast forming a second shape; and imaging said second shape.

67. A comfort device for a mammography unit cassette holder comprising:
a compressible x-ray transparent material configured to define a cavity for containing said mammography unit cassette holder, wherein said x-ray transparent material comprises a first opening adapted to permit a mammography unit cassette to pass therethrough; a second opening adapted to permit a mammography unit to pass therethrough; and a chamber for entrapping a gas; wherein said material substantially conforms to said cassette holder.

68. The comfort device of claim 67 wherein said chamber is between at least approximately 5 millimeters and approximately 20 millimeters thick when said gas is entrapped therein.

* * * * *